United States Patent [19]

Wyler et al.

[11] Patent Number: 4,735,208
[45] Date of Patent: Apr. 5, 1988

[54] SUBDURAL STRIP ELECTRODE FOR DETERMINING EPILEPTOGENIC FOCI

[75] Inventors: Allen R. Wyler, Memphis, Tenn.; David A. Putz, Racine, Wis.

[73] Assignee: Ad-Tech Medical Instrument Corp., Racine, Wis.

[21] Appl. No.: 4,553

[22] Filed: Jan. 9, 1987

[51] Int. Cl.⁴ .................................................. A61B 5/04
[52] U.S. Cl. ..................................... 128/642; 128/731
[58] Field of Search .............................. 128/639-640, 128/642, 748, 783-784, 798, 731-732

[56] References Cited

U.S. PATENT DOCUMENTS

| 3,108,268 | 10/1963 | Uttal | 128/783 X |
|---|---|---|---|
| 3,724,467 | 4/1973 | Avery et al. | 128/784 |
| 3,738,368 | 6/1973 | Avery et al. | 128/784 |
| 4,114,603 | 9/1978 | Wilkinson | 128/748 |
| 4,219,027 | 8/1980 | Lund | 128/642 |
| 4,233,987 | 11/1980 | Feingold | 128/639 |
| 4,308,873 | 1/1982 | Maynard | 128/731 |
| 4,461,304 | 7/1984 | Kuperstein | 128/642 |
| 4,503,860 | 3/1985 | Sams et al. | 128/639 |
| 4,607,644 | 8/1986 | Pohndorf | 128/640 X |
| 4,632,120 | 12/1986 | Sherwin et al. | 128/639 |

FOREIGN PATENT DOCUMENTS

| 0621352 | 8/1978 | U.S.S.R. | 128/784 |
|---|---|---|---|
| 0665889 | 6/1979 | U.S.S.R. | 128/642 |

Primary Examiner—William E. Kamm
Assistant Examiner—Angela D. Sykes
Attorney, Agent, or Firm—Peter N. Jansson, Ltd.

[57] ABSTRACT

An improved subdural strip electrode for determining epileptogenic foci. The strip has a long gradually tapered proximal end portion terminating in a narrow tip from which lead wires extend, allowing withdrawal of the strip electrode without substantial incision. The strip width and thickness are much less than in prior subdural strip electrodes, and the strip may be withdrawn after extended implantation without the need for general surgery. One preferred embodiment includes a reinforced central region along the strip.

19 Claims, 1 Drawing Sheet

SUBDURAL STRIP ELECTRODE FOR DETERMINING EPILEPTOGENIC FOCI

FIELD OF THE INVENTION

This invention is related generally to electrodes for monitoring cortical electrical activity in order to define cortical epileptogenic foci and, more particularly, to subdural strip electrodes for that purpose.

BACKGROUND OF THE INVENTION

Surgical removal of epileptogenic brain is indicated for treatment of many medically refractory focal seizure disorders. One of the important factors in providing good results from such surgery is the degree of accuracy in identifying epileptogenic foci. Various methods have been used in attempting to determine epileptogenic foci, and all, of course, involve sensing of cortical electrical activity using electrical contacts applied in various ways.

Standard scalp contacts have been used for many years, but accurate localization is usually very difficult with recordings obtained from such contacts. Therefore, many epilepsy centers in recent years have used intracranial recording techniques to better define regions of cortical epileptogenicity.

Intracranial recording techniques have used either of two different types of electrodes—intracortical depth electrodes or subdural strip electrodes. The far more commonly used technique of intracranial recording uses intracortical depth electrodes, but other techniques using subdural strip electrodes, first utilized many years ago, have been shown to be relatively safe and valuable alternatives.

The relative safety of subdural strip electrodes lies in the fact that, unlike depth electrodes, they are not invasive of brain tissue. Depth electrodes are narrow, typically cylindrical dielectric structures with contact bands spaced along their lengths. Such electrodes are inserted into the brain in order to establish good electrical contact with different portions of the brain. Subdural strip electrodes, on the other hand, are flat strips supporting contacts spaced along their lengths. Such strip electrodes are inserted between the dura and the brain, along the surface of and in contact with the brain, but not within the brain.

Subdural strip electrodes will be described in greater detail to provide background information necessary for an understanding of this invention. A subdural strip electrode has an elongated flexible dielectric strip within which a plurality of spaced aligned flat contacts and their lead wires are enclosed and supported in place, sandwiched between front and back layers of material forming the dielectric strip. Each flat contact has a face or main contact surface which is exposed by an opening in the front layer of the dielectric strip. Insulated lead wires, one for each contact, are secured within the strip and exit the strip from a proximal end. The dielectric material used in such subdural strip electrodes is a flexible, medically-acceptable material such as silicone.

Subdural strip electrodes have been put in place, used and removed in the following manner, using the surgical steps here described:

An incision is made in the scalp over the site of proposed electrode placement and a standard-sized burr hole is drilled in the skull. A linear incision is then made in the dura across the diameter of the burr hole. Dural tack-up sutures are placed in both dural margins for retraction.

The strip electrode described above is moistened and its tip grasped with forceps. A Penfield dissector or similar implement is used to help pass the electrode strip under the dural edge. The strip, which is usually 5–7 cm in length, is pushed into the space between the dura and the brain until it is completely inserted. Insertion is complete when the proximal end of the subdural strip electrode is beneath the dura. Up to four strip electrodes of the type described are inserted between the dura and the brain, oriented such that their exposed contact discs are on the side of the strip in contact with the surface of the brain. After all strips have been positioned in a burr hole, the dural edges are approximated with a suture.

All wires for each electrode strip are then brought out through the skin by first threading them through a needle and then drawing them through the scalp at a distance (usually 4–5 cm) from the burr hole incision. The lead wires are coded in some manner such that the location of their respective brain contacts is known and the measurements of electrical activity can properly be interpreted. When electrical activity is confirmed, the scalp is closed in layers and a dressing is applied over the burr hole incision. Cortical electrical activity is monitored typically for a period of one to three weeks.

After completion of the period of monitoring, the subdural strip electrodes are, of course, removed. Removal of subdural strip electrodes has required general surgery in the operating room, with the imposition of a general anesthetic. This is a disadvantage in that it is both expensive and difficult for the patient.

The surgical steps for removal of subdural strip electrodes include reopening the burr hole incision and reopening the dura incision. The lead wires are then cut at a location near the proximal end of the electrode strip and removed by outward movement through the needle wounds in the scalp. The body of the strip electrode is then grasped with forceps and removed through the reopened burr hole incision. The incisions are then reclosed and appropriate dressings applied to both the reclosed burr hole incision and needle wound or wounds.

Thus, it can be seen that removal of subdural electrode strips is in itself a major surgical operation. Coming as it does at the end of a long period of brain monitoring, during which the patient is attached to sensing and recording equipment, subdural strip electrode removal has another difficult inconvenience and risk for the patient. Of course, general surgery in the operating room also means that substantial additional costs are incurred right at the end of the entire test procedure.

Addressing the significant problems and disadvantages associated with removal of the subdural strip electrodes of the prior art requires thinking which appears to run contrary to certain normal assumptions.

For one thing, it would seem that proper insertion of the strip electrode requires at least some degree of stiffness (less than complete flexibility) in the strip, because of how such strips are inserted through the burr hole and under the dura. That is, rather than being pulled into place between the dura and brain by grasping the distal end of the strip, such strips obviously must be pushed into place from their proximal ends, from which the lead wires extend. Nothing supports the strip along its length much beyond the edge of the burr hole during the complete insertion step. It is understood that, if there is insufficient stiffness along the strip length and across the strip width, the strip could not be inserted properly. In some cases, it could stray from the intended position; in other cases, it could turn or double up.

Proper insertion and positioning and having an accurate understanding of the exact positions of the strips are essential to proper interpretation of the recordings taken from the strip contacts. For that reason, it has been thought necessary to have a certain amount of strip thickness and width in order to provide the necessary body or stiffness for proper insertion.

Another consideration in the design of subdural strip electrodes is their ability to adequately support the contacts and lead wires secured by the dielectric strip. If insufficient dielectric supporting material encompasses the contacts and lead wires, the lead wires when pulled could distort the strip and create undesirable openings in the strip. The lead wires would also be more prone to break away and the contacts more prone to be mislocated within the strip.

All of these factors argue for greater width and thickness dimensions in the strip electrode—that is, greater cross-sectional area. And, this is particularly the case if the manner of use of the electrode were to require substantial pulling on the lead wires.

The subdural strip electrodes of the prior art with the smallest cross-sectional area are at least about 9.65 mm in width and at least about 0.80 or 0.90 mm thick at their thinnest points. Made of very flexible silicone, such strips, while quite flexible, have enough stiffness or body along their lengths and widths, to allow proper insertion. Reductions to substantially smaller thicknesses, widths and cross-sectional areas would be thought to make the strip unacceptably weak along its length and width for proper insertion. Furthermore, substantial reductions in dimension would be thought to compromise proper securement of contacts and lead wires within the flexible dielectric material forming the body of the strip.

Subdural strip electrodes of the prior art have, at their proximal ends from which their lead wires extend, a variety of rounded and/or partially tapered configurations. Such strip electrodes of the prior art all have substantial shoulders or other irregularities along their proximal ends.

And, at their termination points from which the wires extend such strip electrodes have substantial widths, with or without a common casing tube securing the lead wires firmly to the location of exit from the proximal end. Such substantial widths or casing tubes have been thought essential to hold the lead wires securely in place, the more so if substantial pulling of the lead wires were to be involved.

Given the configuration and dimensioning of subdural strip electrodes, dictated by various considerations including those mentioned above, their removal using the complex and expensive general surgery techniques described above has been deemed essential. There has been a need for an improved subdural strip electrode the removal of which after an extended period of implantation can be carried out more easily, without the need for general surgery.

The subdural strip electrodes of the prior art have, on occasion, been known to penetrate brain tissue inadvertently during insertion. Thus, there has been a need for an improved subdural strip electrode which is less likely to penetrate brain tissue inadvertently during insertion.

OBJECTS OF THE INVENTION

It is an object of this invention to provide an improved subdural strip electrode overcoming some of the problems and shortcomings of the prior art.

Another object of this invention is to simplify the medical procedures necessary for accurate determination of epileptogenic foci.

Another object of this invention is to provide a subdural strip electrode which may be removed from intracranial insertion with simpler techniques than have been used with such electrodes in the past.

Another object of this invention is to provide a strip electrode for intracranial pick-up of cortical electrical activity which provides excellent noninvasive electrical contact with the brain and is removable without general surgery.

Another object of this invention is to provide an improved subdural strip electrode which reduces the possibility of inadvertent invasion of brain tissue during insertion.

These and other important objects will be apparent from the descriptions of this invention which follow.

SUMMARY OF THE INVENTION

The invention is an improved subdural strip electrode for determining epileptogenic foci which overcomes certain problems and deficiencies of prior subdural strip electrodes. The strip electrode of this invention is of the type having an elongated flexible dielectric strip with front and back layers, a plurality of spaced aligned flat contacts sandwiched between the front and back dielectric layers and each having a face exposed by a front-layer opening, and lead wires secured within the strip and exiting the strip from a proximal end portion.

The strip has a pair of opposite edges which, as with prior strip electrodes, are spaced apart by a principal width along a major portion of the strip length which abuts a proximal end portion. However, along the entire proximal end portion the opposite edges extend in long straight converging lines to form a tapered length terminating at a tip from which the wires extend. Such tapered length extends for a distance more than the principal strip width, and preferably for a distance more than one and one-half times the principal strip width.

The principal strip width is less than about 8 mm and preferably less than about 6.5 mm. The tip of the tapered length is of sufficiently narrow width such that withdrawal of the electrode strip after extended implantation can begin without substantial incision. The tip width is preferably less than about 2 mm, and most preferably less than about 1.6 mm. Such strip electrode characteristics allow its withdrawal after extended implantation without the patient's entering general surgery.

The flexible dielectric material used in the improved subdural strip electrode of this invention is a silicone material of the same type used in certain subdural strip electrodes of the prior art. However, the thickness of the strip electrode is substantially reduced. In preferred embodiments, the improved subdural strip electrode of this invention has a thickness along its length varying between about 0.30 mm and about 0.75 mm. In areas away from the lead wires extending along the strip within the dielectric material, the strip has a thickness of less than about 0.5 mm, and most preferably less than about 0.4 mm. In highly preferred embodiments, such strip thickness is on the order of 0.35 mm.

With such reduced width and thickness, the cross-sectional area of the improved subdural strip electrode of this invention is as little as less than one-third the cross-sectional area of prior subdural strip electrodes. Yet, such improved subdural strip electrode may be of the same length—typically on the order of 5-7 cm—and present the same number of contacts and the same contact area for each contact.

Significantly, it has been found that such improved subdural strip electrode may readily be inserted between the dura and the brain without misdirection or doubling back or lack of placement control due to insufficient flexibility either along the length or width of the strip. Also, it is significant that, despite such substantially reduced cross-sectional area and substantially reduced amount of dielectric material enveloping and securing the electrical contacts and lead wires, such lead wires and contacts remain properly in place within the dielectric material, even during the application of substantial pulling force on the strip through the lead wires.

The improved subdural strip electrode of this invention provides important advantages in the insertion and removal procedures required in connection with monitoring a patient's cortical electrical activity to define the location of cortical epileptogenic foci. The most significant advantage is that the improved subdural strip electrode of this invention may be withdrawn after an extended period of implantation without the need to enter general surgery.

Without placing the patient under general anesthesia, the improved subdural strip electrode may be pulled from the head, through the small opening through which the lead wires were threaded during insertion, simply by carefully pulling on the lead wires. At most, the wire passage opening in the scalp may be slightly enlarged to allow the tip of the tapered end portion to enter the opening as withdrawal begins.

As such pulling begins, the tip will thread itself through the still weak dural opening, through the still-covered burr hole, and then through the wire opening in the scalp. As the improved strip electrode is gradually withdrawn, it will stretch the tissues as required and the flexible strip will curl across its width as necessary and/or undergo other deformation as necessary to facilitate such withdrawal.

It has been found that the improved subdural strip electrode of this invention can be withdrawn in this manner with minimal pressure being applied on the head and scalp at the withdrawal site, and without breaking of the lead wires or the strip itself as it passes the burr hole. After such withdrawal, a suitable dressing is applied.

Thus, the need for general surgery at the end of the typical one-to-three week period of electrode implantation may be eliminated. This substantially reduces the cost, inconvenience and distress associated with the lengthy process for defining the location of cortical epileptogenic foci. And, it further enhances the relative desirability of using non-invasive electrodes for intracranial monitoring cortical electrical activity.

As with subdural strip electrodes of the prior art, the improved subdural strip electrode preferably has at least four contacts spaced along its length. In preferred embodiments, the lead wires are bunched in overlying fashion at the tip of the tapered length from which the wires extend. Such overlying bunched arrangement at the tip allows the tip width to be minimized. The dielectric strip alone provides sufficient securement for the wires at the tip. There is no need for any wire encasement or other reinforcement at or beyond the tip of the strip electrode.

As noted, the tapered length at the proximal end portion of the strip electrode extends for a substantial distance. In preferred embodiments, the angle between the substantially straight converging lines and the strip direction (for example, the strip center line) is less than about 22 degrees. This allows withdrawal of the strip electrode to proceed with minimal pressure at the withdrawal site. In the most highly preferred embodiments, such angle is less than about 15 degrees.

The smaller such angle is, the more gradual the application of tissue-stretching pressure at the withdrawal site. However, extending the tapered portion for too great a length could in some cases bring insertion problems. An angle on the order of about 13 degrees has been found to be functionally quite satisfactory.

The straight converging lines forming the tapered length of the strip electrode are critical to proper operation of this invention. The presence of shoulders or other substantial interruptive features along such tapered length would eliminate the possibility of successful and non-traumatic withdrawal of the strip electrode through the dura, the burr hole, under the scalp and through the wire opening without the patient's entering general surgery.

Another advantage of the improved subdural strip electrode of this invention is that it reduces the possibility of invasion of brain tissue during the insertion process. The substantially reduced cross-sectional area of the strip, as mentioned above, surprisingly does not interfere with the ease and accuracy of strip insertion. However, this same lack of strip substantiality (or stiffness) which could have been expected to cause some problems for insertion serves to reduce the possibility of brain invasion.

In certain highly preferred embodiments of this invention, additional dielectric material is included in a center region of the strip along the length of the strip, such center region being where the lead wires are located. Such additional amount of silicone, or other acceptable dielectric material, allows wire securement within the strip to be reinforced. It also minimizes back surface irregularities otherwise present due to the wires within the strip. The back surface of the strip is given a smoother surface.

Another advantage of the improved subdural strip electrode of this invention is that its reduced thickness means that the electrical contact surfaces are recessed to a lesser extent from the front face of the strip. This tends to improve electrical contact with the surface of the brain. And, in embodiments including the aforementioned reinforced central region, such region itself tends to improve electrical contact with the brain by providing properly located pressure behind the contacts.

DETAILED DESCRIPTIONS OF PREFERRED EMBODIMENTS

Figure 1:
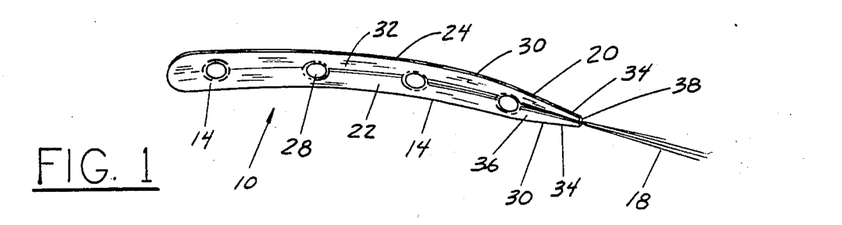
FIG. 1 is a perspective view of the improved subdural strip electrode of this invention.
Figure 2:
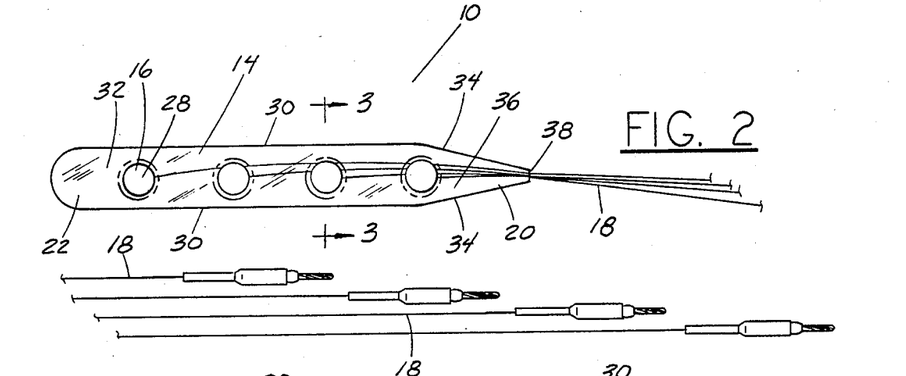
FIG. 2 is an enlarged front view, broken along the lead wires.
Figure 3:
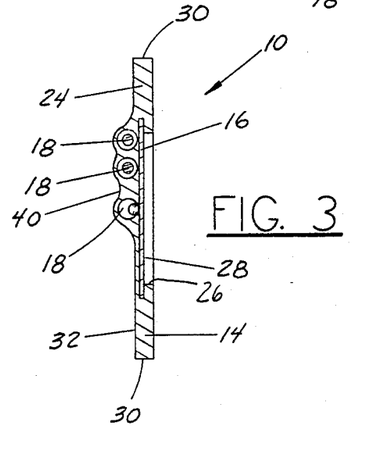
FIG. 3 is a side sectional view taken along section 3—3 as illustrated in FIG. 2.
Figure 4:
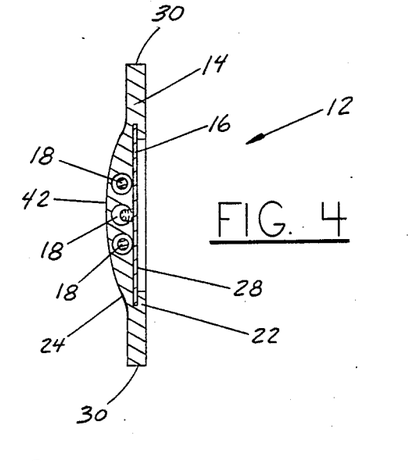
FIG. 4 is a similar side sectional view illustrating an alternate preferred embodiment.
Figure 5:
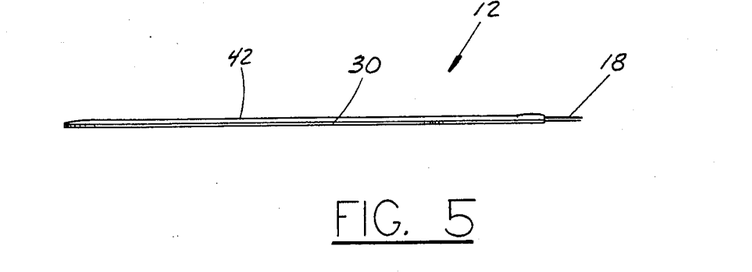
FIG. 5 is side edge view of the embodiment of FIG. 4.

FIGS. 1-3 illustrate an improved subdural strip electrode 10 in accordance with this invention. FIGS. 4-5 illustrate a modified improved subdural strip electrode 12. Each is of the type having an elongated flexible silicone dielectric strip 14, a plurality of spaced aligned flat electrical stainless steel contact disks 16 held within dielectric strip 14, and lead wires 18 exiting strip 14 from a proximal end 20 thereof.

Dielectric strips 14 of strip electrodes 10 and 12 have front and back dielectric layers 22 and 24, respectively. Each front layer 22 has a front layer opening 26 for each contact disk 16. Openings 26 are circular and somewhat smaller in diameter than contact disks 16. Openings 26 serve to expose the faces 28 of contact disks 16. Front and back layers 22 and 24 are sealed together by adhesive and/or heat such that they form, in essence, an integral dielectric strip.

Dielectric strip 14 not only supports and encloses contact disks 16 therein, but supports and encloses lead wires 18. A single lead wire is electrically secured, by solder or otherwise, to each contact disk 16. A preferred number of contact disks 16 for each strip electrode is four, and, thus, four lead wires 18 are used.

Each lead wire is a stainless steel strand which is coated with teflon such that electrical contact is not made with the other contact disks 16 which it passes as it extends to proximal end 20 where it exits dielectric strip 14. The diameter of lead wires 18, including their teflon insulation is on the order of 0.38 mm.

Subdural strip electrodes 10 and 12 each have a pair of opposite edges 30 which, along a major portion 32 of the strip abutting proximal end portion 20, are spaced apart by a fixed principal width. Such principal width is less than about 8 mm, and preferably less than about 6.5 mm. A most preferred with is 6.35 mm (0.25 in.). It has been found that such narrowness of the strip electrode is essential to withdrawal without general surgery. Such greatly simplified withdrawal procedure is easiest with strip width in the preferred range. And, it has been found that, with strip width within the ranges specified, contact disks 16 can present faces 28 of equal dimension to the contact faces of the prior art strip electrodes while still adequately securing such disks and their respective lead wires in place.

Opposite edges 30 extend in straight converging lines 34 at proximal end portion 20 of dielectric strip 14 to form a tapered length 36 of strip 14. Tapered length 36 extends for a distance which is well over one and a half times the principal strip width, such that the tapering is gradual. Furthermore, by virtue of the straightness of converging lines 34, the tapering is smooth.

Tapered length 34 terminates in a tip 38 from which lead wires 18 extend. Tip 38 has a narrow width, which is narrow enough such that withdrawal of the electrode strip after extended implantation can begin without incision, except perhaps minor incision in the wire wound. The entire strip may be withdrawn through the wire wound in the scalp. The width of tip 38, in a direction perpendicular to strip electrodes 10 and 12, is preferably less than about 2.0 mm, and most preferably less than about 1.6 mm.

It has been found that such dimensioning allows the beginning of withdrawal in the convenient manner described, and that the tapering as described allows complete withdrawal of strip electrodes 10 and 12 after extended implantation without the need to enter general surgery. Such tapering allows withdrawal to proceed with minimal pressure applied to the skin at the withdrawal site and with minimal pulling pressure being applied to remove the strip electrode.

As illustrated best in FIGS. 1 and 2, lead wires 18 are bunched together in overlying fashion at tip 38. This allows the width of tip 38 to be minimized, in order to facilitate the beginning of strip electrode withdrawal. Furthermore, no wire encasement is used other than dielectric strip 14 at tip 38. Dielectric strip 14 alone provides securement for lead wires 18 at tip 38.

Converging lines 34 each form an angle to the strip direction of less than about 22 degrees. The most preferred angles between coverging lines 34 and the strip direction are less than about 15 degrees. It has been found that such angles facilitate proper strip withdrawal as described above.

The improved subdural strip electrodes of this invention are substantially thinner than subdural strip electrodes of the prior art. As illustrated best in FIGS. 3 and 4, lead wires 18 form a substantial part of the thickness of the strip electrodes at their thickest portions. The thickness of the strip preferably varies between about 0.30 mm and about 0.75 mm. Whatever the thickness of the thickest part of the strip, which is typically toward the upper end of the aforementioned thickness range, the strips are substantially thinner at portions away from lead wires 18 than at portions adjacent to lead wires 18.

The strip thickness away from wires 18 is preferably less than about 0.5 mm and most preferably less than about 0.4 mm. It has been found that such thinness, along with the aforementioned changes, allows and facilitates removal without entering general surgery without compromising on insertion qualities. And, it has been found that suitable disk and wire securement is possible even if such thickness is in the lower end of the acceptable range.

The dielectric strip 14 is of a material, such as silicone as noted, such that it conforms closely to the wire shapes and serves to hold lead wires 18 and contact disks 16 securely in place. FIG. 3 illustrates that subdural strip electrode 10 has a back surface 40 with substantial surface irregularities due to wires 18.

Such irregularities are eliminated and wire securement within the strip is reinforced in the preferred subdural strip electrode 12, illustrated in FIGURES 4 and 5. Subdural strip electrode 12 has additional dielectric material in a central region 42 extending along the length of the strip. Such additional dielectric material along central region 42 improves wire securement within the strip and minimizes back surface irregularities, without interfering with the improved simplified withdrawal procedures described herein.

A highly preferred silicone material used for dielectric strips 14 is a Silastic sheeting obtained from Dow Chemical Co. of Midland, Mich. The preferred material is Product No. 500-1, and is translucent and non-reinforced. The improved subdural strip electrodes are made using two plys of such material properly cut and using a Type A Dow adhesive.

Contact disks 16 are of very thin stainless steel. A thickness of 0.051 mm has been found very satisfactory. After lead wires 18 are electrically secured to disks 16, the disks and wires are placed properly on one layer of the silicone material using proper adhesive. A second layer of the silicone material is placed thereover to sandwich the wires and contact disks in place. Heat is applied such that the two silicone layers form in essence an integral dielectric web.

Assembly methods do not form a part of this invention. Various other assembly methods could be used.

While the principles of this invention have been described in connection with specific embodiments, it should be understood clearly that these descriptions are made only by way of example and are not intended to limit the scope of the invention.

What is claimed:

1. An improved subdural strip electrode for determining epileptogenic foci of the type having a fully-implantable elongated flexible dielectric strip formed of front and back dielectric layers, spaced aligned flat contacts sandwiched between such layers with faces exposed by front-layer openings, and lead wires secured within and exiting the strip from a proximal end portion, the strip having a pair of opposite edges spaced apart by a principal width along a major portion of the strip length abutting the proximal end portion, the improvement wherein:

the principal strip width is less than about 8 mm;

the opposite edges, along substantially the entire proximal end portion, extend in straight converging lines to form a tapered length terminating at a tip from which the wires extend, said straight converging lines and tapered length extending along a length greater than the principal strip width; and the strip while of a short length accommodating full implantation, has said tip of a width sufficiently narrow so that withdrawal of the strip electrode can begin without substantial incision, whereby the strip electrode is configured and dimensioned such that it may be completely withdrawn after extended implantation without entering general surgery.

2. The subdural strip electrode of claim 1 wherein the principal strip width is less than about 6.5 mm.

3. The subdural strip electrode of claim 1 wherein the tip width is less than about 2.0 mm.

4. The subdural strip electrode of claim 3 wherein the tip width is less than about 1.6 mm.

5. The subdural strip electrode of claim 3 wherein there are a least four contacts and corresponding wires, said wires being bunched in overlying fashion at the tip, said dielectric strip alone providing securement for the wires at the tip.

6. The subdural strip electrode of claim 1 wherein the straight converging edge lines are at an angle to the strip direction of less than about 22 degrees, whereby withdrawal of the strip electrode may proceed with minimal pressure at the withdrawal site.

7. The subdural strip electrode of claim 6 wherein the angle is less than about 15 degrees.

8. The subdural strip electrode of claim 1 wherein additional dielectric material is in a central region along the length of the strip encompassing the wires, whereby wire securement within the strip is reinforced and strip back surface irregularities due to the wires are minimized.

9. The subdural strip electrode of claim 8 wherein the principal strip width is less than about 6.5 mm, the thickness of the strip is within the range of about 0.030 mm to 0.75 mm, with the strip having a thickness away from the wires of less than about 0.40 mm.

10. The subdural strip electrode of claim 9 wherein the tip width is less than about 1.6 mm.

11. The subdural strip electrode of claim 10 wherein there are at least four contacts and corresponding wires, said wires being bunched in overlying fashion at the tip, said dielectric strip alone providing securement for the wires at the tip.

12. The subdural strip electrode of claim 11 wherein the straight converging edge lines are at an angle to the strip direction of less than about 22 degrees, whereby withdrawal of the strip electrode may proceed with minimal pressure at the withdrawal site.

13. The subdural strip electrode of claim 12 wherein the angle is less than about 15 degrees.

14. The subdural strip electrode of claim 1 wherein said straight converging lines and tapered length extends along a length greater than one and one-half times the principal strip width.

15. An improved subdural strip electrode for determining epileptogenic foci of the type having an elongated flexible dielectric strip formed of front and back dielectric layers, spaced aligned flat contacts sandwiched between such layers with faces exposed by front-layer openings, and lead wires secured within and exiting the strip from a proximal end portion, the strip having a pair of opposite edges spaced apart by a principal width along a major portion of the strip length abutting the proximal end portion, the improvement wherein:

the principal strip width is less than about 8 mm and the thickness of the strip is within the range of about 0.30 mm to 0.75 mm;

the opposite edges, along substantially the entire proximal end portion, extend in straight converging lines to form a tapered length terminating at a tip from which the wires extend, said straight converging lines and tapered length extending along a length greater than the principal strip width; and the tip has a width sufficiently narrow so that withdrawal of the strip electrode can begin without substantial incision, whereby the strip electrode is configured and dimensioned such that it may be completely withdrawn after extended implatation without entering general surgery.

16. The subdural strip electrode of claim 15 wherein the strip has a thickness away from the wires of less thn about 0.50 mm.

17. The subdural strip electrode of claim 16 wherein the strip thickness away from the wires is less than about 0.90 mm.

18. An improved subdural strip electrode for determining epileptongenic foci of the type having an elongated flexible dielectric strip formed of front and back dielectric layers, spaced aligned flat contacts sandwiched between such layers with faces exposed by front-layer openings, and lead wires secured within and exiting the strip from a proximal end portion, the strip having a pair of opposite edges spaced apart by a principal width along a major portion of the strip length abutting the proximal end portion, the improvement wherein:

the principal strip width is less than about 8 mm and the thickness of the strip is within the range of about 0.30 mm to 0.75 mm;

the opposite edges, along substantially the entire proximal end portion, extend in straight converging lines to form a tapered length terminating at a tip from which the wires extend, said straight converging lines and tapered length extending along a length greater than the principal strip width;

additional dielectric material is in a central region along the length of the strip, said central region dielectric material encompassing the wires, whereby wire securement within the strip is reinforced and strip back surface irregularities due to the wires are minimized; and the tip having a width sufficiently narrow so that withdrawal of the strip electrode can begin without substantial incision, whereby the strip electrode is configured and dimensioned such that it may be completely withdrawn after extended implantation without entering general surgery.

19. The subdural strip electrode of claim 18 wherein the strip has a thickness away from the wires of less than about 0.40 mm.

* * * * *

UNITED STATES PATENT AND TRADEMARK OFFICE
CERTIFICATE OF CORRECTION

PATENT NO. : 4,735,208
DATED : April 5, 1988
INVENTOR(S) : Allen R. Wyler and David A. Putz It is certified that error appears in the above-identified patent and that said Letters Patent is hereby corrected as shown below:

Column 9, line 45, change "a" to --at--.

Column 9, line 66, change "0.030" to --0.30--.

Column 10, line 46, change "thn" to --than--.

Column 10, line 50, change "0.90" to --0.40--.

Signed and Sealed this

Second Day of August, 1988

Attest:

DONALD J. QUIGG

Attesting Officer

Commissioner of Patents and Trademarks

REEXAMINATION CERTIFICATE (2617th)
United States Patent [19]
Wyler et al.

[11] B1 4,735,208
[45] Certificate Issued Jul. 4, 1995

[54] SUBDURAL STRIP ELECTRODE FOR DETERMINING EPILEPTOGENIC FOCI

[75] Inventors: Allen R. Wyler, Memphis, Tenn.; David A. Putz, Racine, Wis.

[73] Assignee: Ad-Tech Medical Instrument Corporation, Racine, Wis.

Reexamination Request:
No. 90/003,551, Sep. 2, 1994

Reexamination Certificate for:
Patent No.: 4,735,208
Issued: Apr. 5, 1988
Appl. No.: 4,553
Filed: Jan. 9, 1987

[51] Int. Cl.⁶ ............................................. A61B 5/04
[52] U.S. Cl. ........................................ 128/642; 128/731
[58] Field of Search .......................... 128/639–640, 128/642, 748, 731–732; 607/115–116, 129, 139

[56] References Cited
PUBLICATIONS

Wyler Subdural Strip Electrode; Journal of Neurosurgery, vol. 63, No. 1; Jul. 1985.
Wyler et al.; "Subdural Strip Electrodes for Localizing Epileptogenic Foci"; J. Neurosurg.; vol. 60; Jun. 1984; pp. 1195–1200.

*Primary Examiner*—Angela D. Sykes

[57] ABSTRACT

An improved subdural strip electrode for determining epileptogenic foci. The strip has a long gradually tapered proximal end portion terminating in a narrow tip from which lead wires extend, allowing withdrawal of the strip electrode without substantial incision. The strip width and thickness are much less than in prior subdural strip electrodes, and the strip may be withdrawn after extended implantation without the need for general surgery. One preferred embodiment includes a reinforced central region along the strip.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-19 is confirmed.

* * * * *